United States Patent
Waldmann et al.

(10) Patent No.: US 6,689,869 B2
(45) Date of Patent: *Feb. 10, 2004

(54) LABELED HUMANIZED ANTI-CD18 ANTIBODIES AND FRAGMENTS AND KITS COMPRISING SAME

(75) Inventors: Herman Waldmann, Oxford (GB); Martin J. Sims, Comberton (GB); J. Scott Crowe, Letchworth (GB)

(73) Assignee: Cambridge University Technical Services Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,967

(22) Filed: Aug. 23, 1999

(65) Prior Publication Data

US 2003/0185818 A1 Oct. 2, 2003

Related U.S. Application Data

(63) Continuation of application No. 08/465,313, filed on Jun. 5, 1995, now Pat. No. 5,997,867, which is a continuation of application No. 08/182,067, filed on Mar. 26, 1994, now Pat. No. 5,985,279.
(60) Provisional application No. PCT/GB92/01289, filed on Jul. 15, 1992, now Pat. No. 5,985,279.

(30) Foreign Application Priority Data

Jul. 16, 2001 (GB) .............................. 9115364

(51) Int. Cl.⁷ ..................... C07K 16/28; A61K 39/395; G01N 33/53
(52) U.S. Cl. .............................. 530/388.75; 530/387.1; 530/387.3; 530/388.1; 530/388.2; 530/388.22; 530/388.7; 530/388.73; 530/391.1; 530/391.3; 435/7.1; 435/810; 424/130.1; 424/133.1; 424/141.1; 424/143.1; 424/144.1; 424/153.1; 424/154.1; 424/173.1; 424/178.4
(58) Field of Search .......................... 424/130.1, 133.1, 424/144.1, 173.1, 141.1, 153.1, 178.1, 143.1, 154.1; 435/810, 7.1; 530/382.1, 387.3, 388.2, 388.22, 388.73, 388.75, 388.1, 388.7, 391.3, 391.1

(56) References Cited

U.S. PATENT DOCUMENTS

| | | | |
|---|---|---|---|
| 4,797,277 A | 1/1989 | Arfors ........................ | 424/85.8 |
| 4,840,793 A | 6/1989 | Todd, III et al. .......... | 424/85.8 |
| 4,935,234 A | 6/1990 | Todd, III et al. .......... | 424/85.8 |
| 5,019,648 A | 5/1991 | Schlossman et al. ....... | 530/387 |
| 5,147,637 A | 9/1992 | Wright et al. .............. | 424/85.8 |
| 5,219,997 A | 6/1993 | Schlossman et al. .... | 530/388.7 |
| 5,225,539 A | 7/1993 | Winter ..................... | 530/387.3 |
| 5,288,854 A * | 2/1994 | Diamond et al. | |
| 5,310,551 A | 5/1994 | Wegner et al. ............. | 424/85.8 |
| 5,324,510 A | 6/1994 | Wegner et al. ............. | 424/85.8 |
| 5,340,800 A | 8/1994 | Liu et al. .................... | 514/12 |
| 5,475,091 A | 12/1995 | Springer et al. ........ | 530/388.22 |
| 5,585,089 A | 12/1996 | Queen et al. ............. | 424/133.1 |
| 5,693,761 A | 12/1997 | Queen et al. ............. | 536/23.53 |
| 5,693,762 A | 12/1997 | Queen et al. ............. | 530/387.3 |
| 5,821,337 A | 10/1998 | Carter et al. ............. | 530/387.3 |
| 5,858,725 A | 1/1999 | Crowe et al. | |
| 5,859,205 A | 1/1999 | Adair et al. ............. | 530/387.3 |
| 5,888,508 A | 3/1999 | Hildreth .................. | 424/130.1 |
| 5,985,279 A * | 11/1999 | Waldmann et al. | |

FOREIGN PATENT DOCUMENTS

| | | |
|---|---|---|
| EP | 0 328 404 | 8/1989 |
| EP | 0 346 078 | 12/1989 |
| EP | 0 387 701 B1 | 9/1990 |
| EP | 0 438 310 A1 | 7/1991 |
| EP | 0 438 312 A2 | 7/1991 |
| EP | 0 440 351 A2 | 8/1991 |
| EP | 0 578 515 A2 | 1/1994 |
| JP | 6-501614 | 2/1994 |
| WO | WO 89/04174 | 5/1989 |
| WO | WO 90/07861 | 7/1990 |
| WO | WO 90/13316 | 11/1990 |
| WO | WO 90/15076 | 12/1990 |
| WO | WO 91/09967 | 7/1991 |
| WO | WO 92/03473 | 3/1992 |
| WO | WO 92/04034 | 3/1992 |
| WO | WO 92/07075 | 4/1992 |
| WO | WO 92/11870 | 7/1992 |
| WO | WO 92/22653 | 12/1992 |
| WO | WO 94/02175 | 2/1994 |
| WO | WO 94/12214 | 6/1994 |

OTHER PUBLICATIONS

GB9022011.2, filed Oct. 10, 1990, corresponding to a copy of the priority document of WO92/07075 (PCT/GB91/01744; Reference AM4).

Lockwood, C. M., et al., "Anti–adhesion Molecule Therapy as an Interventional Strategy for Autoimmune Inflammation," *Clinical Immunology*, 93(2):93–106 (1999).

Gorman, S.D., et al., "Reshaping a Therapeutic CD4 Antibody," *Proc. Natl. Acad. Sci. USA*, 88 (1):4181–4185 (1991).

Craig, C., "Centocor Gets First Panorex Approval in Germany for Colorectal Cancer," *BioWorld Today*, 6(2): 1–2 (Jan. 5, 1995).

Reichmann, L., et al., "Reshaping Human Antibodies for Therapy," *Nature*, 332: 323–327 (1988).

(List continued on next page.)

*Primary Examiner*—Phillip Gambel
(74) *Attorney, Agent, or Firm*—Hamilton, Brook, Smith & Reynolds, P.C.

(57) ABSTRACT

A humanized antibody or antibody fragment having all or part of the CDRs as defined and capable of binding to the human CD18 antigen. The antibody and fragment may be labeled and are useful in a variety of applications, such as in therapy in treating leukocyte mediated conditions such as inhibiting ingress of leukocytes into the lung and other organs and treatment of inflammation. Also provided is a kit for detecting the presence of human CD18 antigen comprising an antibody or fragment of the invention, which is optionally labeled.

22 Claims, No Drawings

OTHER PUBLICATIONS

Page, M. J., and Sydenham, M.A., "High Level Expression of the Humanized Monoclonal Antibody CAMPATH–1H in Chinese Hamster Ovary Cells," *Bio/Technology,* 9:64–68 (1991).

Carlos, T.M., and Harlan, J.M., "Membrane Proteins Involved in Phagocyte Adherence to Endothelium," *Immunol. Rev.,* 114: 5–28 (1990).

Diamond, M.S., et al., "Differential Effects on Leucocyte Functions of CD11a, CD11b, and CD18 mAb," Knapp, W. et al., Eds., In: *Leukocyte Typing IV, White Cell Differentiation Antigens,* (Oxford University Press: Oxford), 570–574 (1989).

Pope, I., et al., "Epitope Mapping of Rat CD11a/CD18 Antibodies and Comparison with Third and Fourth Workshop Panels," Knapp, W., et al., Eds., In: *Leukocyte Typing IV, White Cell Differentiation Antigens,* (Oxford University Press: Oxford), 559–560 (1989).

Benjamin, R.J., et al., "Tolerance to Rat Monoclonal Antibodies," *J. Exp. Med.,* 163: 1539–1552 (1986).

Chatenoud, L., et al., "Restriction of the Human In Vivo Immune Response against the Mouse Monoclonal Antibody OKT3[1]," *J. Immunol.,* 137(3): 830–838 (1986).

Brüggemann, Marianne, et al., "The Immunogenicity of Chimeric Antibodies," *J. Exp. Med.,* 170: 2153–2157 (1989).

Arfors, K–E., et al., "A Monoclonal Antibody to the Membrane Glycoprotein Complex CD18 Inhibits Polymorphonuclear Leukocyte Accumulation and Plasma Leakage In Vivo," *Blood,* 69:338–340 (1987).

Price, T.H., et al., "In Vivo Inhibition of Neutrophil Function in the Rabbit Using Monoclonal Antibody to CD18," *J. Immunol.,* 139: 4174–4177 (1987).

Vedder, N.B., et al., "A Monoclonal Antibody to the Adherence–promoting Leukocyte Glycoprotein, CD18, Reduces Organ Injury and Improves Survival from Hemorrhagic Shock and Resuscitation in Rabbits," *J. Clin. Invest.,* 81: 939–944 (1988).

Locey, B.J., et al., "The Role of CD11/CD18 Integrin Molecules in Neutrophil and Monocyte Homotypic Adhesion," In: *Leukocyte Typing IV,* W. Knapp, et al., Editors (Oxford: Oxford University Press), 555–558 (1989).

Doerschuk, C.M., et al., "CD18–dependent and –independent Mechanisms of Neutrophil Emigration in the Pulmonary and Systemic Microcirculation of Rabbits," *J. Immunol.,* 144: 2327–2333 (1990).

Mileski, W.J., et al., "Inhibition of CD18–dependent Neutrophil Adherence Reduces Organ Injury after Hemorrhagic Shock in Primates," *Surgery,* 108: 206–212 (1990).

Sharar, S.R., et al., "A CD18 Monoclonal Antibody Increases the Incidence and Severity of Subcutaneous Abscess Formation after High–dose *Staphylococcus aureus* Injection in Rabbits," *Surgery,* 110: 213–220 (1991).

Mulligan, M.S., et al., "Lung Injury after Deposition of IgA Immune Complexes," *J. Immunol.* 148: 3086–3092 (1992).

Eichacker, P.Q., et al., "Leukocyte CD18 Monoclonal Antibody Worsens Endotoxemia and Cardiovascular Injury in Canines with Septic Shock," *J. Appl. Physiol.,* 74: 1885–1892 (1993).

Harris, W.J. and Emery S., "Therapeutic Antibodies—The Coming of Age," *TIBTECH,* 11: 42–44 (1993).

Emery, S.C., and Adair, J.R., "Humanised Monoclonal Antibodies for Therapeutic Applications," *Exp. Opin. Invest. Drugs,* 3(3): 241–251 (1994).

Edgington, S.M., "How Sweet it is: Selectin–Mediating Drugs," *Bio/Technology,* 10: 383–389 (1992).

Sims, M.J., et al., "Humanised CD18 Antibody Can Block Function without Cell Destruction," *J. Immunol.,* 151(4): 2296–2308 (1993).

Daugherty, B.L., et al., "Polymerase Chain Reaction Facilitates the Cloning, CDR–Grafting, and Rapid Expression of a Murine Monoclonal Antibody Directed against the CD18 Component of Leukocyte Integrins," *Nucl. Acids Research,* 19(9): 2471–2476 (1991).

Knapp, W., et al., Eds., *Leukocyte Ty ping IV, White Cell Differentiation Antigens*(Oxford University Press: Oxford, 1079 (1989).

Lewis, A.P. and Crowe, J.S., "Immunoglobulin Complementarity–determining Region Grafting by Recombinant Polymerase Chain Reaction to Generate Humanised Monoclonal Antibodies," *Gene,* 101: 297–302 (1991).

Mountain, A., and Adair, J.R., "Engineering Antibodies for Therapy," *Biotechnology and Genetic Engineering Reviews,* 10: 1, and 10–13 (1992).

Winn, R.K., et al., "Monoclonal Antibodies to Leukocyte and Endothelial Adhesion Molecules Attenuate Ischemia–Reperfusion Injury," *Behring. Inst. Mitt.,* 92: 229–237 (1993).

Ward, P.A., and Mulligan, M.S., "Blocking of Adhesion Molecules in vivo as Anti–inflammatory Therapy," *Therapeutic Immunol.,* 1: 165–171 (1994).

Joliffe, L.K., "Humanized Antibodies: Enhancing Therapeutic Utility Through Antibody Engineering," *Intern. Rev. Immunol.,* 10: 241–250 (1993).

Berzofsky, J.A., and Berkower, I.J., "Immunogenicity and Antigen Structure", Paul, W.E. ed., (Raven Press: NY), In: *Fundamental Immunology,* Chapter 8, p. 242 (1993).

Albelda, S.M., et al., "Adhesion Molecules and Inflammatory Injury," *FASEB J.,* 8:504–512 (1994).

Natanson, C., et al., "Selected Treatment Strategies for Septic Shock Based on Proposed Mechanisms of Pathogenesis," *Ann. Intern. Med.,* 120(9) :771–783 (1994).

* cited by examiner

LABELED HUMANIZED ANTI-CD18 ANTIBODIES AND FRAGMENTS AND KITS COMPRISING SAME

RELATED APPLICATIONS

This application is a continuation of U.S. application Ser. No. 08/465,313, filed Jun. 5, 1995 (now U.S. Pat. No. 5,997,867), which is a continuation of U.S. application Ser. No. 08/182,067, filed Mar. 23, 1994 (now U.S. Pat. No. 5,985,279), which is the U.S. National Phase of International Application No. PCT/GB92/01289, filed Jul. 15, 1992, designating the United States and claiming priority under 35 U.S.C. § 119 to British Application No. GB 9115364.3, filed Jul. 16, 1991. The teachings of all of the foregoing applications are incorporated herein by reference in their entirety

BACKGROUND OF THE INVENTION

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al. ("Sequences of proteins of immunological interest" US Dept. of Health and Human Services, US Government Printing Office, 1987).

The preparation of an altered antibody in which the CDRs are derived from a different species than the framework of the antibody's variable domains is disclosed in EP-A-0239400. The CDRs may be derived from a rat or mouse monoclonal antibody. The framework of the variable domains, and the constant domains, of the altered antibody may be derived from a human antibody. Such a humanized antibody elicits a negligible immune response when administered to a human compared to the immune response mounted by a human against a rat or mouse antibody. Humanized CAMPATH-1 antibody is disclosed in EP-A-0328404 (Campath® antibody is a registered trademark).

SUMMARY OF THE INVENTION

The present invention relates to an antibody which binds to the CD18 antigen, to the preparation of such an antibody and to a pharmaceutical composition which contains the antibody. The invention also relates to methods of using the anti-CD18 antibody.

DETAILED DESCRIPTION OF THE INVENTION

According to one aspect of the present invention, there is provided a humanized antibody in which sufficient of the amino acid sequence of each CDR shown below is provided such that the antibody is capable of binding to the human CD18 antigen:

light chain: CDR1 (SEQ ID NOS: 3 and 4)
    CDR2 (SEQ ID NOS: 5 and 6)
    CDR3 (SEQ ID NOS: 7 and 8)
heavy chain: CDR1 (SEQ ID NOS: 11 and 12)
    CDR2 (SEQ ID NOS: 13 and 14)
    CDR3 (SEQ ID NOS: 15 and 16).

According to another aspect, the invention provides a DNA molecule encoding a humanized antibody in which sufficient of the amino acid sequence of each CDR shown above is provided such that the antibody is capable of binding to the human CD18 antigen.

The antibody preferably has the structure of a natural antibody or a fragment thereof. The antibody may therefore comprise a complete antibody, a (Fab')$_2$ fragment, a Fab fragment, a light chain dimer or a heavy chain dimer. The antibody may be an IgG such as IgG1, IgG2, IgG3 or IgG4; or IgM, IgA, IgE or IgD. The constant domain of the antibody heavy chain may be selected accordingly. The light chain constant domain may be a kappa or lambda constant domain.

The antibody may be a chimeric antibody of the type described in WO 86/01533. A chimeric antibody according to WO 86/01533 comprises an antigen binding region and a non-immunoglobulin region. The antigen binding region is an antibody light chain variable domain and/or heavy chain variable domain. Typically the chimeric antibody comprises both light and heavy chain variable domains. The non-immunoglobulin region is fused to the C-terminus of the antigen binding region. The non-immunoglobulin region is typically a non-immunoglobulin protein and may be an enzyme region, a region derived from a protein having known binding specificity, from a protein toxin or indeed from any protein expressed by a gene. The non-immunoglobulin region may be a carbohydrate region. The two regions of the chimeric antibody may be connected via a cleavable linker sequence.

The light chain CDRs 1 to 3 and heavy chain CDRs 1 to 3 of SEQ ID NOS: 3 to 8 and SEQ ID NOS: 11 to 16, respectively, are the CDRs of the YFC51.1.1 rat antibody which is a CD18 antibody. The specificity of a humanized antibody for the human CD18 antigen can be determined by flow cytometry, monocyte adhesion and/or by T-cell proliferation assays as follows:

Monocyte (MNC) Adhesion

MNC's are treated with the phorbol diester PDBu ($10^{-9}$ M) in the presence and absence of antibody (20 µl) for 5 minutes. These cells are then transferred to bovine aortic endothelial cell (BAEC) monolayers and incubated for 30 minutes in a humidified atmosphere of 95% air, 5% $CO_2$ at 37° C. Non-adherent cells are removed by washing in phosphate buffered saline (PBS) three times. The adherent cells are then lysed in situ with 50 µl of 0.5% hexadecyltrimethyl ammonium bromide. Dianisidine dihydrochloride (0.63 mM) containing 0.4 mM hydrogen peroxide is added (250 µl) to each well and incubated for a further 10 minutes. Enzyme activity is then assessed using the presence of monocyte-specific myeloperoxidase, recorded as an increase in absorbance. The optical density of the samples can then be recorded at 450 nm using a multi-well plate reader (Anthos series, Lab Teck instruments). Comparisons can then be made between treated and untreated samples (Bath et al., *J. Immunol Meth.*, 118: 59–65 (1989)).

Flow Cytometry

Surface labeling of rat, rabbit, guinea-pig and human monocytes with antibody is carried out according to the method of Gladwin et al., (*Biochim. Biophys. Acta*, 1052: 166–172 (1990)). Briefly, 1 ml aliquots of a cell suspension ($5 \times 10^6$) are incubated with the appropriate antibody, monodispersed and incubated on melting ice for 30 minutes. The cells are twice washed in PBS and incubated for a further 30 minutes with a 1:200 dilution of rabbit anti-rat F(ab')$_2$ FITC conjugate on melting ice. The cells are finally washed three times in PBS and fixed in 0.1% para-formaldehyde. Analysis of surface labeling can be performed using an Epics Elite flow cytometer (Coulter cytometry, Hialeah, Fla.) using standard computer, electronics and optics. The Elite is configured with a 15 mW 488 nm Argon-ion laser (Cyonics model 2201, San Jose, Calif.). Monocyte and lymphocyte populations are separated by forward angle light scatter and side scatter. Green fluorescence data for $2 \times 10^4$ monocytes is collected using bit-map gating and collected on a three decade log scale. Green fluorescence data for $2 \times 10^4$ neutrophils is collected in a similar manner. For each sample, mean fluorescence intensity in the presence of the primary mAb is compared with cells incubated with rabbit anti-rat F(ab')$_2$ FITC fragments alone and the percentage labeling of the cells determined. Samples can be labeled in triplicate and repeat experiments can be performed on three separate occasions.

T-cell Proliferation Assay

Human mononuclear cells are prepared from defibrinated blood using density gradient separation over Ficoll-paque® solution. Lymphocytes ($2 \times 10^5$ cells) are cultured in each well of a flat bottomed 96-well microtitre plate (Nunclon, Roskild, Denmark), in RPMI 1640 supplemented with 10% autologous serum, 2 mM glutamine and 100 iU penicillin/ 100 $\mu$g ml$^{-1}$ streptomycin. Triplicate cultures are set up with the medium alone or with antigen (Tetanus Toxoid, 3 $\mu$g ml$^{-1}$) or mitogen (PHA, 1 $\mu$g ml$^{-1}$), in the presence or absence of different concentrations of monoclonal antibodies. Cells are cultured at 37° C. in a humidified atmosphere of 95% air, 5% CO$_2$ for five days. Wells are then pulsed with 1 $\mu$Ci [methyl$^3$H] thymidine (2Ci mmol$^{-1}$, Amersham), harvested 18 hours later and radioactivity counted by liquid scintillation using a B counter (LKB, Betaplate, Sweden). The results are expressed as mean+/−SEM.

Suitably, the CDRs of a humanized antibody are the light chain CDRs 1 to 3 and the heavy chain CDRs 1 to 3 above. The amino acid sequences of these CDRs may be changed, however. The amino acid sequence of each CDR may be changed by up to 40% by amino acid substitutions, insertions and/or deletions, for example by up to 30%, up to 20% or up to 10%.

Each CDR may therefore include one or two amino acid substitutions, insertions and/or deletions. There may be up to three amino acid substitutions, insertions, and/or deletions in light chain CDR. Up to four amino acid substitutions, insertions and/or deletions may be present in light chain CDR1 or heavy chain CDR3. Up to six amino acid substitutions, insertions and/or deletions may be present in heavy chain CDR2. Preferably the amino acid sequence of each CDR is substantially homologous to that of each CDR of YFC 51.1.1.

The framework and the constant domains of the antibody are human framework and human constant domains. Preferably the framework of the variable region of the antibody heavy chain is substantially homologous to the corresponding framework of the human protein NEWM (Saul et al., *J. Biol. Chem.* 25: 585–597 (1987)). Homology in respect of the framework is generally 80% or more with respect to NEWM, for example 90% or more or 95% or more. A number of amino acid substitutions, insertions and/or deletions may be present. Candidate framework changes that may be made to restore binding include changes of amino acid residues 27, 30, 48, 66, 67, 71, 91, 93 and 94. The amino acid numbering is according to Kabat et al.

The framework of the variable region of the antibody light chain is typically substantially homologous to the variable domain framework of the protein REI (Epp et al., *Eur. J. Biochem.* 45: 513–524 (1974)). Homology in respect of the framework is generally 80% or more with respect to REI, for example 90% or more or 95% or more. A number of amino acid substitutions, insertions and/or deletions may be present, for example at amino acid residue 71 according to the numbering of Kabat et al.

A humanized antibody is prepared according to the invention by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains.

The first and second expression vectors may be the same vector. The invention further provides:
  a DNA sequence encoding the light chain or the heavy chain of the humanized antibody;
  an expression vector which incorporates a said DNA sequence; and
  a host transformed with a said expression vector.

Each chain of the antibody may be prepared by CDR replacement. The CDRs of a variable region of a light or heavy chain of a human antibody are replaced by sufficient of the amino acid sequence of each CDR of the rat antihuman CD18 antibody YFC51.1.1 such that the resulting antibody is capable of binding to the CD18 antigen. The CDR-encoding regions of DNA encoding a hypervariable region of a human antibody chain are replaced by DNA encoding the desired CDRs. If appropriate, this altered DNA is linked to DNA encoding a constant domain for the antibody chain. The DNA is cloned into an expression vector. The expression vector is introduced into a compatible host cell which is cultured under such conditions that the antibody chain is expressed. Complementary antibody chains which are co-expressed in this way may then assemble to form the humanized antibody.

The present invention is described herein with particular reference to the production of a humanized antibody having CDRs derived directly or indirectly from the rat antibody YFC51.1.1. However, the techniques described herein can equally be used to derive other humanized anti-CD18 antibodies. According to a further aspect, the present invention provides a humanized (CDR grafted) anti-CD18 antibody.

There are four general steps to humanize a monoclonal antibody. These are:
  (1) determining the nucleotide and predicted amino acid sequence of the starting antibody light and heavy variable domains;
  (2) designing the humanized antibody, i.e., deciding which antibody framework region to use during the humanizing process;

(3) the actual humanizing methodologies/techniques; and (4) the transfection and expression of the humanized antibody.

Step 1: Determining the Nucleotide and Predicted Amino Acid Sequence of the Antibody Light and Heavy Chain Variable Domains To humanize an antibody only the amino acid sequence of antibody's heavy and light chain variable domains needs to be known. The sequence of the constant domains is irrelevant because these do not contribute to the reshaping strategy. The simplest method of determining an antibody's variable domain amino acid sequence is from cloned cDNA encoding the heavy and light chain variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains. In the present instance, the nucleotide sequence and predicted amino acid sequence of the light and heavy chains of the rodent YFC51.1.1 antibody are shown in SEQ ID NOS: 1 and 2 and SEQ ID NOS: 9 and 10.

Step 2: Designing the Humanized Antibody

There are several factors to consider in deciding which human antibody sequence to use during the humanization. The humanization of light and heavy chains are considered independently of one another, but the reasoning is basically similar for each.

This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognize antigen. Thus the substitution of rodent CDRs into a human variable domain framework is most likely to result in retention of their correct spatial orientation if the human variable domain framework is highly homologous to the rodent variable domain from which they originated. A human variable domain should preferably be chosen therefore that is highly homologous to the rodent variable domain(s). A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.

2. List the human antibody variable domain sequences and compare for homology. Primarily the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanization.

Step 3: The Actual Humanizing Methodologies/Techniques

An antibody may be humanized by grafting the desired CDRs onto a human framework according to EP-A-0239400. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanization may be achieved using the recombinant polymerase chain reaction (PCR) methodology of WO 92/07075. Using this methodology, a CDR may be spliced between the framework regions of a human antibody.

In general, the technique of WO 92/07075 can be performed using a template comprising two human framework regions, AB and CD, and between them, the CDR which is to be replaced by a donor CDR. Primers A and B are used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Step 4: The Transfection and Expression of the Reshaped Antibody

Following the mutagenesis reactions to reshape the antibody, the mutagenized DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanized antibody of the invention;

(b) preparing a second replicable expression vector including a suitable promoter operably linked to a DNA sequence which encodes at least the variable domain of a complementary Ig light or heavy chain, respectively;

(c) transforming a cell line with the first or both prepared vectors; and (d) culturing said transformed cell line to produce said altered antibody.

Preferably the DNA sequence in step (a) encodes both the variable domain and the or each constant domain of the human antibody chain. The humanized antibody can be prepared using any suitable recombinant expression system. The cell line which is transformed to produce the altered antibody may be a Chinese Hamster Ovary (CHO) cell line or an immortalized mammalian cell line, which is advantageously of lymphoid origin, such as a myeloma, hybridoma, trioma or quadroma cell line. The cell line may also comprise a normal lymphoid cell, such as a B-cell, which has been immortalized by transformation with a virus, such as the Epstein-Barr virus. Most preferably, the immortalized cell line is a myeloma cell line or a derivative thereof.

The CHO cells used for expression of the antibodies according to the invention may be dihydrofolate reductase (dhfr) deficient and so dependent on thymidine and hypoxanthine for growth (Urlaub et al., *Proc. Natl. Acad. Sci. U.S.A.*, 77: 4216–4220 (1980)). The parental dhfr CHO cell line is transfected with the DNA encoding the antibody and dhfr which enables selection of CHO cell transformants of dhfr positive phenotype. Selection is carried out by culturing the colonies on media devoid of thymidine and hypoxanthine, the absence of which prevents untransformed cells from growing and transformed cells from resalvaging the folate pathway and thus bypassing the selection system. These transformants usually express low levels of the DNA of interest by virtue of co-integration of transfected DNA of interest and DNA encoding dhfr. The expression levels of the DNA encoding the antibody may be increased by amplification using methotrexate (MTX). This drug is a direct inhibitor of the enzyme dhfr and allows isolation of resistant colonies which amplify their dhfr gene copy number sufficiently to survive under these conditions. Since the DNA sequences encoding dhfr and the antibody are closely linked in the original transformants, there is usually concomitant amplification, and therefore increased expression of the desired antibody.

Another preferred expression system for use with CHO or myeloma cells is the glutamine synthetase (GS) amplification system described in WO 87/04462. This system involves the transfection of a cell with DNA encoding the enzyme GS and with DNA encoding the desired antibody. Cells are then selected which grow in glutamine free medium and can thus be assumed to have integrated the DNA encoding GS. These selected clones are then subjected to inhibition of the enzyme GS using methionine sulphoximine (Msx). The cells, in order to survive, will amplify the DNA encoding GS with concomitant amplification of the DNA encoding the antibody.

Although the cell line used to produce the humanized antibody is preferably a mammalian cell line, any other suitable cell line, such as a bacterial cell line or a yeast cell line, may alternatively be used. In particular, it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be recovered and purified according to standard procedures of the art, including ammonium sulfate precipitation, affinity columns, column chromatography, gel electrophoresis and the like (See, generally, Scopes, R., *Protein Purification*, Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, a humanized antibody may then be used therapeutically or in developing and performing assay procedures, immunofluorescent stainings, and the like (See, generally, *Immunological Methods*, Vols. I and II, Lefkovits and Pernis, eds., Academic Press, New York, N.Y. (1979 and 1981)).

The humanized anti-CD18 antibodies can be used for example in the treatment of leukocyte mediated conditions. The humanized anti-CD18 antibodies typically find use in inhibiting influx of leukocytes into the lungs and other organs during sepsis or other infectious or non-infectious trauma. The humanized anti-CD18 antibody can therefore be used for inhibiting the ingress of leukocytes into the lung and other organs in patients having endotoxic shock or adult respiratory distress syndrome. The antibody can be used to treat asthma or leukocyte-mediated reperfusion damage post thrombolytic therapy, to treat inflammation in the lung and other organs in patients having an inflammation caused by sepsis or other infectious or non-infectious trauma, to eliminate or reduce inflammation in a patient being administered with an anti-infective agent or to assist in the administration of a therapeutic drug to a patient during chemotherapy (EP-A-0346078).

The humanized antibodies of the present invention may also be used in combination with other antibodies, particularly human monoclonal antibodies reactive with other markers on cells responsible for the disease. For example, suitable T-cell markers can include those grouped into the so-called "Clusters of Differentiation" as named by the First International Leukocyte Differentiation Workshop, *Leukocyte Typing*, Bernard et al., Eds., Springer-Verlag, N.Y. (1984).

The antibodies can also be used as separately administered compositions given in conjunction with chemotherapeutic or immunosuppressive agents. Typically, the agents will include cyclosporin A or a purine analog (e.g., methotrexate, 6-mercaptopurine, or the like), but numerous additional agents (e.g., cyclophosphamide, prednisone, etc.) well-known to those skilled in the art may also be utilized.

An antibody of the present invention may form part of an immunotoxin. Immunotoxins are characterized by two components and are particularly useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known within the art, and can be found, for example in "Monoclonal Antibody-Toxin Conjugates: Aiming the Magic Bullet", Thorpe et al., *Monoclonal Antibodies in Clinical Medicine*, Academic Press, pp. 168–190 (1982).

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatin; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). See, generally, "Chimeric Toxins," Olsnes and Phil, *Pharmac. Ther.*, 25: 335–381 (1982), and "Monoclonal Antibodies for Cancer Detection and Therapy," eds. Baldwin and Byers, pp. 159–179, 224–266, Academic Press (1985).

The delivery component of the immunotoxin is a humanized antibody according to the present invention. Intact immunoglobulins or their binding fragments, such as Fab, are preferably used. Typically, the antibodies in the immunotoxins will be of the human IgA, IgM or IgG isotype, but other mammalian constant regions may be utilized as desired.

The invention further provides a pharmaceutical composition comprising a pharmaceutically acceptable carrier or diluent and, as active ingredient, a humanized antibody according to the invention. The composition may comprise an immunotoxin according to the invention. The humanized antibody, immunotoxin and pharmaceutical compositions thereof of this invention are particularly useful for parenteral administration, i.e., subcutaneously, intramuscularly or intravenously.

The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, *Remington's Pharmaceutical Science*, 15th ed., Mack Publishing Company, Easton, Pa. (1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human-like antibodies or a cocktail thereof can be administered for prophylactic and/or therapeutic treatments. In therapeutic application, compositions are administered to a patient already suffering from a disease, in an amount sufficient to cure or at least partially arrest or alleviate the disease and its complications. An amount adequate to accomplish this is defined as a "therapeutically effective dose." Amounts effective for this use will depend upon the severity of the infection and the general state of the patient's own immune system, but generally range from about 1 to about 200 mg of antibody per dose, with dosages of from 5 to 25 mg per patient being more commonly used. It must be kept in mind that the materials of the invention may generally be employed in serious disease states, that is life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies.

In prophylactic applications, compositions containing the present antibodies or a cocktail thereof are administered to a patient not already in a disease state to enhance the patient's resistance. Such an amount is defined to be a "prophylactically effective dose". In this use, the precise amounts again depend upon the patient's state of health and general level of immunity, but generally range from 0.1 to 25 mg per dose, especially 0.5 to 2.5 mg per patient. A preferred prophylactic use is for the prevention of kidney transplant rejection.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Human-like antibodies of the present invention can further find a wide variety of utilities in vitro. By way of example, the exemplary antibodies can be utilized for T-cell typing, for isolating specific CD18 antigen-bearing cells or fragments of the receptor, for vaccine preparation, or the like.

For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject antibodies in the protection against or detection of a cellular activity or for the presence of a selected antigen. Thus, a humanized antibody of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assay, this will usually be present in a separate vial. The second antibody is typically conjugated to a label and formulated in an analogous manner with the antibody formulations described above. The kit will generally also include a set of instructions for use.

The following Example illustrates the invention.

EXAMPLE

Cloning and Sequencing of the YFC51.1.1 Rat Anti-human CD18 Heavy and Light Chains Total RNA was isolated from $2.5 \times 10^7$ YFC51.1.1 expressing cells following the method of Chomczynski and Sacchi (*Anal. Biochem.*, 162: 156–159 (1987)), using 1 ml of extraction solution per $1 \times 10^7$ cells. The resulting RNA pellet was redissolved in 50 µl diethyl pyrocarbonate (DEPC)-treated distilled water, and spectrophotometrically determined to be at a concentration of 4 µg/µl. Dynabeads® Oligo $(dT)_{25}$ microspheres (Dynal) were used to extract mRNA from 75 µg total RNA employing the manufacturer's protocol.

cDNA was synthesized from the isolated MRNA and cloned into the plasmid pSPORT-1 using the SUPER-SCRIPT Plasmid System for cDNA Synthesis and Plasmid Cloning kit (BRL) following the method recommended by the manufacturer. *Escherichia coli* MAX EFFICIENCY DH5α Competent Cells (BRL) were transformed with the resulting cDNA/pSPORT-1 ligation. Approximately 5000 colonies were lifted onto Hybond®-N nylon filters (Amersham) and lysed, denatured and fixed following the method of Buluwela et al. (*Nucleic Acids Res.*, 17: 452 (1989)). The filters were treated with proteinase K (50 µg/ml) in 0.2×SSC, 0.1% SDS at 55° C. for 30 min, and then excess debris removed with a tissue.

(i) Heavy Chain

An oligonucleotide as shown in SEQ ID NO: 17 complementary to a portion of rat gamma-CH 1 constant region (bases 496–515) was end-labeled and used to screen the filters for YFC51.1.1 heavy chain following the standard protocols. Approximately 50 potential positive colonies were detected, and 20 selected for further analysis. Plasmid DNA was prepared using the method of Del Sal et al. (*Nucleic Acids Res.*, 16: 9878 (1988)) and 12 of the 20 contained inserts of the expected size for rat immunoglobulin heavy chain cDNA. A clone, p51H.6, was selected, and the variable region was sequenced in both directions by plasmid priming following the dideoxy chain termination method (Sanger et al., (*Proc. Natl. Acad. Sci., USA*, 74: 5463–5467 (1977)), according to the Sequenase® DNA Sequencing kit (USB) protocol. The sequence of the variable region is shown in SEQ ID NOS: 9 and 10.

(ii) Light Chain

A clone of the rat myeloma Y3-Ag 1.2.3 light chain (Crowe et al., *Nucleic Acids Res.*, 17: 7992 (1989)) was labeled with digoxigenin-11-dUTP using the Nonradioactive DNA labeling and Detection Kit (Boehringer Mannheim) and used to screen the filters for the YFC51.1.1 light chain, following the manufacturer's protocol. Approximately 40 potential positive colonies were detected, and 24 selected for further analysis. Plasmid DNA was prepared as described above. Both Y3-Ag 1.2.3 and YFC51.1.1 light chains were isolated (Y3 cell line being hybridoma fusion partner) but were distinguishable by having different restriction patterns. One clone, p51L.4, containing the YFC51.1.1 light chain was chosen and sequenced as described for the heavy chain. The sequence of the variable region is shown in SEQ ID NOS: 1 and 2.

Designing the Humanized Antibody

Using the selection procedure described in Step (2) above, the human variable domain frameworks of the NEWM heavy chain and REI light chain (Kabat et al., 1987) were chosen for the humanization process.

Construction of the Humanized Heavy and Light Chain Genes

The humanized heavy and light chains were constructed following the method of Lewis and Crowe (*Gene*, 101: 297–302 (1991)).

(i) Light Chain

Light chain oligonucleotide primers:

$A_L$: SEQ ID NO: 18;
$B_L$: SEQ ID NO: 19;
$C_L$: SEQ ID NO: 20;
$D_L$: SEQ I) NO:21;
$E_L$: SEQ ID NO:22;
$F_L$: SEQ ID NO:23;
$G_L$: SEQ ID NO:24;
$H_L$: SEQ ID NO:25.

PCR reactions (Saiki et al., *Science*, 239: 487–491 (1988)) were performed in a programmable heating block (Hybaid) using 20 rounds of temperature cycling (94° C. for 1 min, 50° C. for 2 min, and 72° C. for 3 min) followed by a final 10 min step at 72° C. 1 µg of each primer, a specified amount of template, and 2.5 units of *Taq* polymerase (Perkin Elmer Cetus) were used in a final volume of 100 µl with the reaction buffer as recommended by the manufacturer.

The initial template for the PCR was CAMPATH-1H light chain (humanized CAMPATH-1 on REI framework; Page and Sydenham, *BioTechnology*, 9: 64–68 (1991)). Four initial PCR reactions were carried out, with 10 ng of template per reaction, using the primer pairs $A_L$ (SEQ ID NO:18) with $B_L$ (SEQ ID NO:19), $C_L$ (SEQ ID NO:20) with $D_L$ (SEQ ID NO:21), $E_L$ (SEQ ID NO:22) with $F_L$ (SEQ ID NO:23), and $G_L$ (SEQ ID NO:24) with $H_L$ (SEQ ID NO:25) respectively. The products of these PCR reactions, fragments $AB_L$, $CD_L$, $EF_L$ and $GH_L$, respectively, were purified using Prep-A-Gene (Bio-Rad® Laboratories) following the protocol recommended by the manufacturer. Fragments $AB_L$, with $CD_L$ and $EF_L$ with $GH_L$ were combined using a quarter of each purified product, and subjected to recombinant PCR reactions with primers $A_L$ (SEQ ID NO:18) plus $D_L$ (SEQ ID NO:21), and $E_L$ (SEQ ID NO:22) plus $H_L$ (SEQ ID NO:25) respectively. The products of these reactions, fragments $AD_L$ and $EH_L$, were purified as above, and a quarter of each combined in a recombinant PCR reaction using primers $A_L$ (SEQ ID NO:18) and $H_L$ (SEQ ID NO:25). The final humanized light chain recombinant PCR product, $AH_L$, was cloned into the HindIII site of pUC-18 (BRL) following the method of Crowe et al., *Nucleic Acids Res.*, 19: 184 (1991), using the HindIII sites in primers $A_L$ (SEQ ID NO:18) and $H_L$ (SEQ ID NO:25). Plasmid isolates were sequenced by the dideoxy chain termination method, and clones of the correct sequence chosen.

(ii) Heavy Chain

Heavy chain oligonucleotide primers:

$A_H$: SEQ ID NO: 26;
$B_H$: SEQ ID NO: 27;
$C_H$: SEQ ID NO: 28;
$D_H$: SEQ ID NO: 29;
$E_H$: SEQ ID NO: 30;
$F_H$: SEQ ID NO: 31;
$G_H$: SEQ ID NO: 32;
$H_H$: SEQ ID NO: 33.

The initial template for the PCR was CAMPATH-1H heavy chain. The rodent CDRs were grafted on to the template following the recombinant PCR method as described above, but using oligonucleotide primers $A_H$ to $H_H$ (SEQ ID NOS:26–33). The final PCR, i.e. fragments $AD_H$ and $EH_H$ with primers $A_H$ (SEQ ID NO:26) and $H_H$ (SEQ ID NO:33), did not give a high yield of product so a fragment $AF_H$ was generated (from fragments $AD_H$ and $EF_H$) and used with fragment $EH_H$ in a PCR with primers $A_H$ (SEQ ID NO:26) and $H_H$ (SEQ ID NO:33). Oligonucleotides $A_H$ (SEQ ID NO:26) and $H_H$ (SEQ ID NO:33) were designed with HindIII and EcoRI sites respectively to enable initial cloning of the humanized variable region, and a SpeI site was introduced into the NEWM framework 4 (FR4) region of oligonucleotide $G_H$ (SEQ ID NO:32) to facilitate subsequent cloning of the variable region with a suitable constant region of choice. The SpeI site was chosen so as not to alter the leucine residue at position 109 (numbering according to Kabat et al., 1987) of the humanized heavy chain template. Four out of the six human heavy J-minigenes possess a leucine at this position (Kabat et al., 1987). Thus the use of the engineered SpeI site should be generally applicable.

The humanized heavy chain variable region recombinant PCR product was cloned into HinDIII/EcoRI-cut pUC-18 (BRL), and plasmid isolates of the correct sequence were chosen. The FR4 and γ1 constant regions of CAMPATH-1H heavy chain were PCR cloned into pUC-18 (BRL) using oligonucleotide primers $X_H$ (SEQ ID NO: 34) and $Y_H$ (SEQ ID NO: 35). Primer $X_H$ (SEQ ID NO:34) contains SpeI and HinDIII sites, and $Y_H$ (SEQ ID NO:35) contains an EcoRI site. The HinDIII and EcoRI sites were used to clone the PCR product into pUC-18, and plasmid isolates of the correct sequence were selected. The complete heavy chain was subsequently reconstituted from the humanized variable region and γ1 constant region clones using the engineered FR4 SpeI site.

Transient Expression in COS Cells

DNA encoding the humanized heavy and light chains were cloned into the vectors pEE6.hCMV and pEE12 respectively, see Stephens and Cockett, *Nucleic Acids Res.*, 17: 7110 (1989); Bebbington et al., *BioTechnology*, 10: 169 (1992); and Bebbington and Hentschel in Glover ed., DNA Cloning Volume III, Academic Press (1987). The vector pEE12 is a pBR322-based vector containing the h-CMV-MEI promoter and the hamster glutamine synthetase (GS) cDNA under control of the SV40 early region promoter. The vector pEE12 corresponds to pEE6 (see EP-A-0338841) with the GS cDNA expression cassette driven by the SV40 promoter transcribing in the same direction as the h-CMV-MEI promoter. Cells transfected with the vectors pEE6, hCMV and pEE12 are capable of growth in glutamine free medium because of the presence of the GS cDNA. As the selection is only on the pEE12 plasmid, effective expression relies upon co-integration of both plasmids.

The recombinant plasmids (5 μg of each) were transfected into 5×10⁵ COS-1 cells using the Transfectam® reagent (Promega, Southampton, U.K.) under the conditions recommended by the manufacturer. Stock COS-1 cells (source ECACC, Porton Down, U.K.) were maintained in DMEM medium (Flow, Irvine, U.K.) supplemented with 10% fetal calf serum (APP, Dudley, U.K.). COS cell transfections were carried out in DMEM medium (Flow, Irvine, U.K.). Growth media from COS-1 cells four days post transfection were assayed by a sandwich ELISA assay using flexible microtiter plates (Falcon, Becton-Dickinson, Plymouth, U.K.) coated with polyclonal anti-human IgG (Sigma, Poole, U.K.) as capture antibody. The assay sample was added and detection performed with an anti-human IgG γ chain-specific peroxidase conjugate (Seralab, Crawley Down, U.K.) and ortho-phenylene dimine-HCl (Sigma, Poole U.K.) as substrate.

The humanized antibody was shown to be expressed transiently in the COS cells by using the spent COS cell supernatant to surface label MF-14 (a T-cell clone) cells for FACS analysis according to the method of Gladwin et al., *Biochem. Biophys. Acta*, 1052: 166–172 (1990). Briefly, 100 μl aliquots of a cell suspension (10⁵) were incubated with the appropriate antibody (spent COS cell supernatant) and incubated on melting ice for 30 minutes. The cells were washed twice in PBS and incubated for a further 30 minutes with the appropriate second antibody (see below). The cells were washed again and 1:50 dilutions of anti-rat Ig-FITC or anti-human Ig-FITC conjugates were added on melting ice. Finally, the cells were washed three times in PBS and fixed in 0.1% paraformaldehyde. Analysis of surface labeling was performed using a Becton-Dickenson FACScan™ flow cytometer using standard computer, electronics and optics.

The humanized antibody in the COS cell supernatant was shown to bind MF-14 cells as well as inhibiting the binding of the rat YFC51.1.1 monoclonal antibody. Since the humanized antibody was shown to have retained binding for CD18 by blocking the binding of the rat monoclonal antibody, stable NSO transfectants were generated.

Stable Expression in NSO Cells

A single expression vector for generating stable transfectants of NSO cells was generated by cloning the complete heavy chain expression cassette from pEE6 into the BamHI site of the pEE12-light chain plasmid. Thus both heavy and light chain coding sequences are transcribed in the same direction from the same vector. 40 μg of plasmid for transfection was linearized by digestion with SalI restriction enzyme that has a recognition sequence within the bacterial plasmid sequence. The linearized DNA was precipitated from solution using ethanol, washed in 70% ethanol, dried and resuspended in sterile water.

Exponentially growing NSO cells (a Human myeloma cell line; see Jarvis, *Methods in Enzymol.*, 73B: 3 (1981); source ECACC, Porton Down, U.K.) were maintained in non-selective DMEM medium (i.e. without glutamine and ferric nitrate but with sodium pyruvate at 110 mg/L (GIBCO/BRL, Paisley, U.K.) supplemented with 1×non-essential amino acids (Flow, Irvine, U.K.) 2 mM glutamine (Gibco) and 10% fetal calf serum (APP, Dudley, U.K.). NSO cells were centrifuged, washed and re-suspended in cold PBS, such that after the addition of the DNA the cells would be at a concentration of 10⁷ cells/ml. The linearized plasmid DNA, 40 μg, was added to 10⁷ cells in an electroporation cuvette on ice. The cells and DNA were mixed gently so as to avoid generating bubbles and the mixture was left on ice for 5 minutes. The outside of the cuvette was wiped dry and two consecutive pulses at 1500V, 3 mF were delivered using a Gene Pulser® electorporator (Bio-Rad® Laboratories). The cuvette was returned to ice for 5 minutes.

Transfected cells were transferred to 96 well plates at densities of 3×10⁵, 7.5×10⁴ and 1.5×10⁴ cells/ml in 50 μl of non-selective medium and incubated at 37° C. for 24 hours. Subsequently 100 μl of selective DMEM medium (i.e. without glutamine and ferric nitrate but with sodium pyruvate at 100 mg/L (GIBCO/BRL, Paisley, U.K.) supplemented with glutamate (60 mg/ml), asparagine (60 mg/ml; Sigma, Poole, U.K.), 1×non-essential amino acids, 7 mg/L of adenosine, cytidine, guanosine and uridine, 2.4 mg/L of thymidine (Sigma, Poole, U.K.) and 10% dialyzed fetal calf serum (APP, Dudley U.K.)) was added to selected clones which had integrated the transfected plasmid. The plates were returned to the incubator and left until substantial cell death had occurred and discrete surviving colonies had appeared. Once colonies of glutamine-independent transfectants could be seen, wells with single colonies were selected and spent tissue culture supernatants were collected and assayed for human IgG secretion.

Wells with single colonies that were positive for IgG secretion were then expanded in culture using selective medium. The cells were distributed in 96 well plates at $10^4$ cells/well in 100 µl of medium and incubated overnight. 100 µl of selective medium containing a concentration of L-methionine sulphoximine (MSX) was added. MSX is a toxic glutamine analogue that allows for selection of vector amplification. Each 96-well plate had a different final concentration of MSX, ranging from 200 µM down to 12.5 µM. Individual colonies were isolated from each independent transfectant at the highest MSX concentration at which MSX resistance occurred. The colonies were expanded and antibody secretion rate (in µg/$10^6$ cells/day) was compared with the unamplified rate. Clones were obtained that expressed the humanized antibody at 1 to 3 µg/$10^6$ cells/day.

The humanized antibody was purified from spent tissue culture supernatant by affinity chromatography over a Superose® protein-G column (Pharmacia) and used in T-cell proliferation assays and C1q binding studies.

T-cell Proliferation

Peripheral human mono-nuclear cells were isolated from defibrinated whole human blood using Lymphoprep® lymphocyte separation chemical (Nycomed, Oslo, Norway) and following the manufacturer's protocol. Triplicate cultures were set up in 96 well flat bottomed microtiter plates (Nunclon, Roskild, Denmark) with the medium clone (RPMI 1640 supplemented with 10% autologous serum, 2 mM glutamine and 100 IU/ml penicillin, 100 µg/ml streptomycin) or with medium and antigen (Tetanus toxoid, 5 µg/ml) or medium and mitogen (PHA, 5 µg/ml), in the presence or absence of YFC 51.1.1 or the humanized antibody. Cells were cultured at 37° C. in a humidified atmosphere of 95% air, 5% $CO_2$ for five days. Wells were then pulsed with 1 µCi [methyl $^3$H] thymidine (2Ci/mmol, Amersham), harvested 4 hours later and radioactivity counted by liquid scintillation using a β counter (LKB, Betaplate, Sweden).

Both the rat YFC51.1.1 monoclonal antibody and the humanized antibody strongly inhibited the antigen specific T-cell response but had little effect on the PHA induced proliferation. However, at high levels of antibody (50 µg/ml) and low levels of PHA (2.5 µg/ml) up to 80% inhibition could be obtained.

Complement Binding

Human mononuclear cells (prepared as above) were stimulated with PHA at 5 µg/ml and incubated at 37° C. for 3 days. The PHA was removed by washing the cells in PBS. The cells were then incubated with 10 g/ml of test antibody for 20 minutes on ice, cells washed in ice cold PBS and incubated with ice cold human serum for 20 minutes. The human serum was removed by washing in ice cold PBS. The cells were then incubated for 20 minutes with a fluoreceinated polyclonal sheep anti-human C1q. Unbound anti-C1q was removed by washing cells in PBS and cells were analyzed on a Becton-Dickenson FACScan™ flow cytometer. YFC51.1.1 was found to bind human C1q weakly and no binding was detected for the humanized antibody. Potential therapeutic uses for anti-CD18 antibodies rely on transient inhibition of CD18-mediated adherence of leukocytes rather than depletion of CD18 positive cells. Accordingly the inability of the humanized antibody to fix human complement on CD18 positive cells is an advantage since it suggests that in vivo the antibody will not deplete using complement but will function as a blocking antibody.

FACS Analysis

A CD18 positive T-cell clone (MF14) was used to determine the binding of humanized compared with rat antibody. Cells were incubated with rat or humanized antibody for 30 minutes on ice. Unbound antibody was removed by washing and the second antibody was added (i.e. rat antibody was added to cells pre-incubated with humanized antibody and vice versa) and incubated for 30 minutes on ice. Cells were washed to remove unbound antibody and a FITC-labeled anti-human or anti-rat antibody added. Unbound label was removed by washing and the cells were analyzed on a Becton-Dickinson FACScan™ flow cytometer. Pre-incubation of MF14 cells with 10 µg/ml of YFC51.1.1 antibody completely blocked the binding of 0.1 µg/ml of humanized antibody. In the reciprocal experiment, preincubation with 10 µg/ml of humanized antibody completely blocked the binding of 0.1 µg/ml YFC51.1.1. In both cases, use of 1.0 and 0.1 µg/ml of the first antibody led to a titration of blocking.

What is claimed is:

1. A labeled humanized antibody or fragment, wherein said antibody or fragment specifically binds to human CD18 antigen and wherein the complementarity determining regions (CDR1, CDR2 and CDR3) of the light chain variable region and the complementarity determining regions (CDR1, CDR2 and CDR3) of the heavy chain variable region have the following amino acid sequences:
light chain:
  CDR1 (SEQ ID NO: 4)
  CDR2 (SEQ ID NO: 6)
  CDR3 (SEQ ID NO: 8)
heavy chain:
  CDR1 (SEQ ID NO: 12)
  CDR2 (SEQ ID NO: 14)
  CDR3 (SEQ ID NO: 16),
wherein said humanized antibody or fragment is labeled.

2. A labeled humanized antibody or fragment of claim 1, wherein said antibody or fragment is labeled with a label selected from the group consisting of a radionuclide, a fluor, an enzyme label, an enzyme substrate, enzyme cofactor, enzyme inhibitor and a hapten.

3. A labeled humanized antibody or fragment thereof which specifically binds to human CD18 antigen wherein said humanized antibody or fragment is labeled and the complementarity determining regions (CDRs) have the following amino acid sequences:
light chain:
  CDR1 (SEQ ID NO:4)
  CDR2 (SEQ ID NO:6)
  CDR3 (SEQ ID NO:8)
heavy chain:
  CDR1 (SEQ ID NO:12)
  CDR2 (SEQ ID NO:14)
  CDR3 (SEQ ID NO:16),
and wherein the variable domain framework of the light chain is derived from the variable domain framework of the protein REI and the variable domain framework of the heavy chain is derived from the variable domain framework of the protein NEWM.

4. A labeled humanized antibody or fragment of claim 3, wherein said antibody or fragment is labeled with a label selected from the group consisting of a radionuclide, a fluor, an enzyme label, an enzyme substrate, enzyme cofactor, enzyme inhibitor and a hapten.

5. A kit for detecting the presence of human CD18 antigen, said kit comprising a humanized antibody or fragment wherein said antibody or fragment specifically binds to human CD1 8 antigen and wherein the complementarity determining regions (CDR1, CDR2 and CDR3) of the light chain variable region and the complementarity determining regions (CDR1, CDR2 and CDR3) of the heavy chain variable region have the following amino acid sequences:

light chain:
    CDR1 (SEQ ID NO:4)
    CDR2 (SEQ ID NO:6)
    CDR3 (SEQ ID NO:8)
heavy chain:
    CDR1 (SEQ ID NO:12)
    CDR2 (SEQ ID NO:14)
    CDR3 (SEQ ID NO:16).

6. The kit of claim 5, further comprising a second antibody reactive with said humanized antibody or fragment.

7. The kit of claim 5, further comprising a second antibody reactive with said humanized antibody or fragment, wherein said second antibody is labeled.

8. A kit for detecting the presence of human CD18 antigen, said kit comprising a humanized antibody or fragment thereof which specifically binds to human CD18 antigen wherein the complementarity determining regions (CDRs) have the following amino acid sequences:

light chain:
    CDR1 (SEQ ID NO:4)
    CDR2 (SEQ ID NO:6)
    CDR3 (SEQ ID NO:8)
heavy chain:
    CDR1 (SEQ ID NO:12)
    CDR2 (SEQ ID NO:14)
    CDR3 (SEQ ID NO:16), and wherein the variable domain framework of the light chain is derived from the variable domain framework of the protein REI and the variable domain framework of the heavy chain is derived from the variable domain framework of the protein NEWM.

9. The kit of claim 8, further comprising a second antibody reactive with said humanized antibody or fragment.

10. The kit of claim 8, further comprising a second antibody reactive with said humanized antibody or fragment, wherein said second antibody is labeled.

11. The kit of claim 7, wherein said second antibody is labeled with a label selected from the group consisting of a radionuclide, a fluor, an enzyme label, an enzyme substrate, enzyme cofactor, enzyme inhibitor and a hapten.

12. The kit of claim 10, wherein said second antibody is labeled with a label selected from the group consisting of a radionuclide, a fluor, an enzyme label, an enzyme substrate, enzyme cofactor, enzyme inhibitor and a hapten.

13. A kit for detecting the presence of human CD18 antigen, said kit comprising a labeled humanized antibody or fragment which specifically binds to human CD18 antigen wherein said antibody or fragment is labeled and the complementarity determining regions (CDR1, CDR2 and CDR3) of the light chain variable region and the complementarity determining regions (CDR1, CDR2 and CDR3) of the heavy chain variable region have the following amino acid sequences:

light chain:
    CDR1 (SEQ ID NO:4)
    CDR2 (SEQ ID NO:6)
    CDR3 (SEQ ID NO:8)
heavy chain:
    CDR1 (SEQ ID NO:12)
    CDR2 (SEQ ID NO:14)
    CDR3 (SEQ ID NO:16).

14. The kit of claim 13, wherein said labeled humanized antibody or fragment is labeled with a label selected from the group consisting of a radionuclide, a fluor, an enzyme label, an enzyme substrate, enzyme cofactor, enzyme inhibitor and a hapten.

15. The kit of claim 13, further comprising a second antibody reactive with said humanized antibody or fragment.

16. The kit of claim 13, further comprising a second antibody reactive with said humanized antibody or fragment, wherein said second antibody is labeled.

17. The kit of claim 16, wherein said second antibody is labeled with a label selected from the group consisting of a radionuclide, a fluor, an enzyme label, an enzyme substrate, enzyme cofactor, enzyme inhibitor and a hapten.

18. A kit for detecting the presence of human CD18 antigen, said kit comprising a labeled humanized antibody or fragment which specifically binds to human CD18 antigen wherein said antibody or fragment is labeled and the complementarity determining regions (CDRs) have the following amino acid sequences:

light chain:
    CDR1 (SEQ ID NO:4)
    CDR2 (SEQ ID NO:6)
    CDR3 (SEQ ID NO:8)
heavy chain:
    CDR1 (SEQ ID NO:12)
    CDR2 (SEQ ID NO:14)
    CDR3 (SEQ ID NO:16), and wherein the variable domain framework of the light chain is derived from the variable domain framework of the protein REI and the variable domain framework of the heavy chain is derived from the variable domain framework of the protein NEWM.

19. The kit of claim 18, wherein said labeled humanized antibody or fragment is labeled with a label selected from the group consisting of a radionuclide, a fluor, an enzyme label, an enzyme substrate, enzyme cofactor, enzyme inhibitor and a hapten.

20. The kit of claim 18, further comprising a second antibody reactive with said humanized antibody or fragment.

21. The kit of claim 18, further comprising a second antibody reactive with said humanized antibody or fragment, wherein said second antibody is labeled.

22. The kit of claim 21, wherein said second antibody is labeled with a label selected from the group consisting of a radionuclide, a fluor, an enzyme label, an enzyme substrate, enzyme cofactor, enzyme inhibitor and a hapten.

\* \* \* \* \*

UNITED STATES PATENT AND TRADEMARK OFFICE
CERTIFICATE OF CORRECTION

PATENT NO. : 6,689,869 B2
DATED : February 10, 2004
INVENTOR(S) : Herman Waldmann, Martin J. Sims and J. Scott Crowe It is certified that error appears in the above-identified patent and that said Letters Patent is hereby corrected as shown below:

Title page,
Item [63], delete "Mar. 26, 1994" and insert -- Mar. 23, 1994 --;
Item [60], delete all text;
Item [30], delete "Jul. 16, 2001" and insert -- July 16, 1991 --.

Signed and Sealed this

Twenty-third Day of November, 2004

JON W. DUDAS
*Director of the United States Patent and Trademark Office*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 375 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
      (A) ORGANISM: Rattus rattus (ix) FEATURE:
      (A) NAME/KEY: CDS
      (B) LOCATION: 1..375

(D) OTHER INFORMATION: /product= "Variable region light
                chain"
                /standard_name= "YFC51.1.1"

(ix) FEATURE:
            (A) NAME/KEY: misc_signal
            (B) LOCATION: 1..60
            (D) OTHER INFORMATION: /function= "Signal sequence"

(ix) FEATURE:
            (A) NAME/KEY: misc_feature
            (B) LOCATION: 130..162
            (D) OTHER INFORMATION: /function= "CDR 1"

(ix) FEATURE:
            (A) NAME/KEY: misc_feature
            (B) LOCATION: 208..228
            (D) OTHER INFORMATION: /function= "CDR 2"

(ix) FEATURE:
            (A) NAME/KEY: misc_feature
            (B) LOCATION: 325..351
            (D) OTHER INFORMATION: /function= "CDR 3"

(xi) SEQUENCE DESCRIPTION: SEQ ID NO:1:

```
ATG AGG GTC CAG GTT CAG TTT CTG GGG CTC CTT CTG CTC TGG ACA TCA        48
Met Arg Val Gln Val Gln Phe Leu Gly Leu Leu Leu Leu Trp Thr Ser
 1               5                  10                  15

GGT GCC CAG TGT GAT GTC CAG ATG ACC CAG TCT CCG TCT TAT CTT GCT        96
Gly Ala Gln Cys Asp Val Gln Met Thr Gln Ser Pro Ser Tyr Leu Ala
            20                  25                  30

GCG TCT CCT GGA GAA AGT GTT TCC ATC AGT TGC AAG GCA AGT AAG AGC       144
Ala Ser Pro Gly Glu Ser Val Ser Ile Ser Cys Lys Ala Ser Lys Ser
        35                  40                  45

ATT AGC AAT TAT TTA GCC TGG TAT CAA CAG AAA CCT GGG GAA GCA AAT       192
Ile Ser Asn Tyr Leu Ala Trp Tyr Gln Gln Lys Pro Gly Glu Ala Asn
    50                  55                  60

AAA CTT CTT GTC TAT TAT GGG TCA ACT TTG CGA TCT GGA ATT CCA TCG       240
Lys Leu Leu Val Tyr Tyr Gly Ser Thr Leu Arg Ser Gly Ile Pro Ser
65                  70                  75                  80

AGG TTC AGT GGC AGT GGA TCT GGT ACA GAT TTC ACT CTC ACC ATC AGA       288
Arg Phe Ser Gly Ser Gly Ser Gly Thr Asp Phe Thr Leu Thr Ile Arg
                85                  90                  95

AAC CTG GAG CCT GCA GAT TTT GCA GTC TAC TAC TGT CAA CAG TAT TAT       336
Asn Leu Glu Pro Ala Asp Phe Ala Val Tyr Tyr Cys Gln Gln Tyr Tyr
            100                 105                 110

GAA AGA CCG CTC ACG TTC GGT TCT GGG ACC AAG CTG GAG                   375
Glu Arg Pro Leu Thr Phe Gly Ser Gly Thr Lys Leu Glu
        115                 120                 125
```

(2) INFORMATION FOR SEQ ID NO:2:

(i) SEQUENCE CHARACTERISTICS:
            (A) LENGTH: 125 amino acids
            (B) TYPE: amino acid
            (D) TOPOLOGY: linear (ii) MOLECULE TYPE: protein (xi) SEQUENCE DESCRIPTION: SEQ ID NO:2:

```
Met Arg Val Gln Val Gln Phe Leu Gly Leu Leu Leu Leu Trp Thr Ser
 1               5                  10                  15

Gly Ala Gln Cys Asp Val Gln Met Thr Gln Ser Pro Ser Tyr Leu Ala
            20                  25                  30

Ala Ser Pro Gly Glu Ser Val Ser Ile Ser Cys Lys Ala Ser Lys Ser
        35                  40                  45
```

```
Ile Ser Asn Tyr Leu Ala Trp Tyr Gln Gln Lys Pro Gly Glu Ala Asn
    50                  55                  60

Lys Leu Leu Val Tyr Tyr Gly Ser Thr Leu Arg Ser Gly Ile Pro Ser
 65              70                  75                  80

Arg Phe Ser Gly Ser Gly Ser Gly Thr Asp Phe Thr Leu Thr Ile Arg
                 85                  90                  95

Asn Leu Glu Pro Ala Asp Phe Ala Val Tyr Tyr Cys Gln Gln Tyr Tyr
            100                 105                 110

Glu Arg Pro Leu Thr Phe Gly Ser Gly Thr Lys Leu Glu
        115                 120                 125

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Rattus rattus (ix) FEATURE:
        (A) NAME/KEY: misc_feature
        (B) LOCATION: 1..33
        (D) OTHER INFORMATION: /function= "CDR 1"

(ix) FEATURE:
        (A) NAME/KEY: CDS
        (B) LOCATION: 1..33

(xi) SEQUENCE DESCRIPTION: SEQ ID NO:3:

AAG GCA AGT AAG AGC ATT AGC AAT TAT TTA GCC                     33
Lys Ala Ser Lys Ser Ile Ser Asn Tyr Leu Ala
 1               5                  10

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:4:

Lys Ala Ser Lys Ser Ile Ser Asn Tyr Leu Ala
 1               5                  10

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Rattus rattus (ix) FEATURE:
        (A) NAME/KEY: misc_feature
        (B) LOCATION: 1..21
        (D) OTHER INFORMATION: /function= "CDR 2"

(ix) FEATURE:
```

```
              (A) NAME/KEY: CDS
              (B) LOCATION: 1..21

(xi) SEQUENCE DESCRIPTION: SEQ ID NO:5:

TAT GGG TCA ACT TTG CGA TCT                                              21
Tyr Gly Ser Thr Leu Arg Ser
  1               5

(2) INFORMATION FOR SEQ ID NO:6:

(i) SEQUENCE CHARACTERISTICS:
              (A) LENGTH: 7 amino acids
              (B) TYPE: amino acid
              (D) TOPOLOGY: linear (ii) MOLECULE TYPE: protein (xi) SEQUENCE DESCRIPTION: SEQ ID NO:6:

Tyr Gly Ser Thr Leu Arg Ser
  1               5

(2) INFORMATION FOR SEQ ID NO:7:

(i) SEQUENCE CHARACTERISTICS:
              (A) LENGTH: 27 base pairs
              (B) TYPE: nucleic acid
              (C) STRANDEDNESS: double
              (D) TOPOLOGY: linear (ii) MOLECULE TYPE: cDNA (vi) ORIGINAL SOURCE:
              (A) ORGANISM: Rattus rattus (ix) FEATURE:
              (A) NAME/KEY: misc_feature
              (B) LOCATION: 1..27
              (D) OTHER INFORMATION: /function= "CDR 3"

(ix) FEATURE:
              (A) NAME/KEY: CDS
              (B) LOCATION: 1..27

(xi) SEQUENCE DESCRIPTION: SEQ ID NO:7:

CAA CAG TAT TAT GAA AGA CCG CTC ACG                                      27
Gln Gln Tyr Tyr Glu Arg Pro Leu Thr
  1               5

(2) INFORMATION FOR SEQ ID NO:8:

(i) SEQUENCE CHARACTERISTICS:
              (A) LENGTH: 9 amino acids
              (B) TYPE: amino acid
              (D) TOPOLOGY: linear (ii) MOLECULE TYPE: protein (xi) SEQUENCE DESCRIPTION: SEQ ID NO:8:

Gln Gln Tyr Tyr Glu Arg Pro Leu Thr
  1               5

(2) INFORMATION FOR SEQ ID NO:9:

(i) SEQUENCE CHARACTERISTICS:
              (A) LENGTH: 417 base pairs
              (B) TYPE: nucleic acid
              (C) STRANDEDNESS: double
              (D) TOPOLOGY: linear (ii) MOLECULE TYPE: cDNA
```

(vi) ORIGINAL SOURCE:
    (A) ORGANISM: Rattus rattus (ix) FEATURE:
    (A) NAME/KEY: CDS
    (B) LOCATION: 1..417
    (D) OTHER INFORMATION: /product= "Heavy chain variable
        region with signal sequence"
        /standard_name= "YFC51.1.1"

(ix) FEATURE:
    (A) NAME/KEY: misc_signal
    (B) LOCATION: 1..57
    (D) OTHER INFORMATION: /function= "Signal sequence"

(ix) FEATURE:
    (A) NAME/KEY: misc_feature
    (B) LOCATION: 148..162
    (D) OTHER INFORMATION: /function= "CDR 1"

(ix) FEATURE:
    (A) NAME/KEY: misc_feature
    (B) LOCATION: 205..255

(ix) FEATURE:
    (A) NAME/KEY: misc_feature
    (B) LOCATION: 352..384

(xi) SEQUENCE DESCRIPTION: SEQ ID NO:9:

```
ATG AAA TGC AGC TGG ATC AAC CTC TTC TTG ATG GCA CTA GCT TCA GGG      48
Met Lys Cys Ser Trp Ile Asn Leu Phe Leu Met Ala Leu Ala Ser Gly
 1               5                  10                  15

GTC TAC GCA GAA GTG CAG CTG CAA CAG TCT GGG CCC GAG CTT CGG AGA      96
Val Tyr Ala Glu Val Gln Leu Gln Gln Ser Gly Pro Glu Leu Arg Arg
             20                  25                  30

CCT GGG TCC TCA GTC AAG TTG TCT TGT AAG ACT TCT GGC TAC AGC ATT     144
Pro Gly Ser Ser Val Lys Leu Ser Cys Lys Thr Ser Gly Tyr Ser Ile
         35                  40                  45

AAA GAT TAC CTT CTG CAC TGG GTA AAA CAT AGG CCA GAA TAC GGC CTG     192
Lys Asp Tyr Leu Leu His Trp Val Lys His Arg Pro Glu Tyr Gly Leu
     50                  55                  60

GAA TGG ATA GGA TGG ATT GAT CCT GAG GAT GGT GAA ACA AAG TAT GGT     240
Glu Trp Ile Gly Trp Ile Asp Pro Glu Asp Gly Glu Thr Lys Tyr Gly
 65                  70                  75                  80

CAG AAG TTT CAA AGC AGG GCC ACA CTC ACT GCA GAT ACA TCC TCC AAC     288
Gln Lys Phe Gln Ser Arg Ala Thr Leu Thr Ala Asp Thr Ser Ser Asn
                 85                  90                  95

ACA GCC TAC ATG CAA CTC AGC AGC CTG ACG TCT GAC GAC ACA GCA ACC     336
Thr Ala Tyr Met Gln Leu Ser Ser Leu Thr Ser Asp Asp Thr Ala Thr
            100                 105                 110

TAT TTT TGT ACT AGA GGC GAA TAT AGA TAC AAC TCG TGG TTT GAT TAC     384
Tyr Phe Cys Thr Arg Gly Glu Tyr Arg Tyr Asn Ser Trp Phe Asp Tyr
        115                 120                 125

TGG GGC CAA GGC ACT CTG GTC ACT GTC TCT TCA                         417
Trp Gly Gln Gly Thr Leu Val Thr Val Ser Ser
    130                 135
```

(2) INFORMATION FOR SEQ ID NO:10:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Cys Ser Trp Ile Asn Leu Phe Leu Met Ala Leu Ala Ser Gly

```
            1               5              10                15
        Val Tyr Ala Glu Val Gln Leu Gln Gln Ser Gly Pro Glu Leu Arg Arg
                         20              25              30

Pro Gly Ser Ser Val Lys Leu Ser Cys Lys Thr Ser Gly Tyr Ser Ile
                     35              40              45

Lys Asp Tyr Leu Leu His Trp Val Lys His Arg Pro Glu Tyr Gly Leu
             50              55              60

Glu Trp Ile Gly Trp Ile Asp Pro Asp Gly Glu Thr Lys Tyr Gly
         65              70              75              80

Gln Lys Phe Gln Ser Arg Ala Thr Leu Thr Ala Asp Thr Ser Ser Asn
                         85              90              95

Thr Ala Tyr Met Gln Leu Ser Ser Leu Thr Ser Asp Asp Thr Ala Thr
                        100             105             110

Tyr Phe Cys Thr Arg Gly Glu Tyr Arg Tyr Asn Ser Trp Phe Asp Tyr
                    115             120             125

Trp Gly Gln Gly Thr Leu Val Thr Val Ser Ser
            130             135
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Rattus rattus (ix) FEATURE:
        (A) NAME/KEY: misc_feature
        (B) LOCATION: 1..15
        (D) OTHER INFORMATION: /function= "CDR 1"

(ix) FEATURE:
        (A) NAME/KEY: CDS
        (B) LOCATION: 1..15

(xi) SEQUENCE DESCRIPTION: SEQ ID NO:11:

```
GAT TAC CTT CTG CAC                                              15
Asp Tyr Leu Leu His
 1               5
```

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Tyr Leu Leu His
 1               5
```

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
    (A) ORGANISM: Rattus rattus (ix) FEATURE:
    (A) NAME/KEY: misc_feature
    (B) LOCATION: 1..51
    (D) OTHER INFORMATION: /function= "CDR 2"

(ix) FEATURE:
    (A) NAME/KEY: CDS
    (B) LOCATION: 1..51

(xi) SEQUENCE DESCRIPTION: SEQ ID NO:13:

```
TGG ATT GAT CCT GAG GAT GGT GAA ACA AAG TAT GGT CAG AAG TTT CAA      48
Trp Ile Asp Pro Glu Asp Gly Glu Thr Lys Tyr Gly Gln Lys Phe Gln
 1               5                  10                  15

AGC                                                                   51
Ser
```

(2) INFORMATION FOR SEQ ID NO:14:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:14:

```
Trp Ile Asp Pro Glu Asp Gly Glu Thr Lys Tyr Gly Gln Lys Phe Gln
 1               5                  10                  15

Ser
```

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Rattus rattus (ix) FEATURE:
        (A) NAME/KEY: misc_feature
        (B) LOCATION: 1..33
        (D) OTHER INFORMATION: /function= "CDR 3"

(ix) FEATURE:
        (A) NAME/KEY: CDS
        (B) LOCATION: 1..33

(xi) SEQUENCE DESCRIPTION: SEQ ID NO:15:

```
GGC GAA TAT AGA TAC AAC TCG TGG TTT GAT TAC                           33
Gly Glu Tyr Arg Tyr Asn Ser Trp Phe Asp Tyr
 1               5                  10
```

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:16:

Gly Glu Tyr Arg Tyr Asn Ser Trp Phe Asp Tyr
 1               5                   10

(2) INFORMATION FOR SEQ ID NO:17:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Rattus rattus (xi) SEQUENCE DESCRIPTION: SEQ ID NO:17:

AGTGGATAGA CAGATGGGGC                                          20

(2) INFORMATION FOR SEQ ID NO:18:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

GATCAAGCTT CTCTACAGTT ACTGAGCACA                                30

(2) INFORMATION FOR SEQ ID NO:19:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:19:

GCTAAATAAT TGCTAATGCT CTTACTTGCT TTACAGGTGA TGG                 43

(2) INFORMATION FOR SEQ ID NO:20:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

AGAGCATTAG CAATTATTTA GCCTGGTACC AGCAGAAGCC AGG                43

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:21:

AGATCGCAAA GTTGACCCAT AGTAGATCAG CAGCTTTGGA G                  41

(2) INFORMATION FOR SEQ ID NO:22:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

TATGGGTCAA CTTTGCGATC TGGTGTGCCA AGCAGATTCA G                  41

(2) INFORMATION FOR SEQ ID NO:23:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:23:

CGTGAGCGGT CTTTCATAAT ACTGTTGGCA GTAGTAGGTG GCGATGT            47

(2) INFORMATION FOR SEQ ID NO:24:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

```
CAACAGTATT ATGAAAGACC GCTCACGTTC GGCCAAGGGA CCAAGGT                    47
```

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:25:

```
GATCAAGCTT CTAACACTCT CCCCTGTTGA                                      30
```

(2) INFORMATION FOR SEQ ID NO:26:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

```
TGGGATCGAT CAAGCTTTAC AGTTACTGAG C                                    31
```

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:27:

```
GTGCAGAAGG TAATCGGTGA AGGTGAAGCC AGACAC                               36
```

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

```
GATTACCTTC TGCACTGGGT GAGACAGCCA CCTGGA                               36
```

(2) INFORMATION FOR SEQ ID NO:29:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:29:

ATACTTTGTT TCACCATCCT CAGGATCAAT CCATCCAATC CACTCAAGAC CTCG      54

(2) INFORMATION FOR SEQ ID NO:30:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:30:

GGTGAAACAA AGTATGGTCA GAAGTTTCAA AGCAGAGTGA CAATGCTGGT AGAC      54

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:31:

CCACGAGTTG TATCTATATT CGCCTCTTGC ACAATAATAG ACCGC      45

(2) INFORMATION FOR SEQ ID NO:32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:32:

AGATACAACT CGTGGTTTGA TTACTGGGGT CAAGGCTCAC TAGTCACAGT CTCC      54

(2) INFORMATION FOR SEQ ID NO:33:

(i) SEQUENCE CHARACTERISTICS:

```
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:33:

TAGAGTCCTG AGGGAATTCG GACAGCCGGG AAGGTG                                36

(2) INFORMATION FOR SEQ ID NO:34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GCTGCTCCTT TTAAGCTTTG GGGTCAAGGC TCACTAGTCA CAGTCTCC                   48

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:35:

AAGCTTCCGT CGAATTCATT TACCCGGAGA CAG                                   33
```